United States Patent
Ryu et al.

(10) Patent No.: US 11,602,623 B2
(45) Date of Patent: Mar. 14, 2023

(54) BALLOON CATHETER HAVING MICRO NEEDLES AND MANUFACTURING METHOD FOR THE SAME

(71) Applicant: INDUSTRY-ACADEMIC COOPERATION FOUNDATION YONSEI UNIVERSITY, Seoul (KR)

(72) Inventors: Won Hyoung Ryu, Goyang-si (KR); Kang Ju Lee, Seoul (KR)

(73) Assignee: INDUSTRY-ACADEMIC COOPERATION FOUNDATION YONSEI UNIVERSITY, Seoul (KR)

(*) Notice: Subject to any disclaimer, the term of this patent is extended or adjusted under 35 U.S.C. 154(b) by 926 days.

(21) Appl. No.: 16/407,531

(22) Filed: May 9, 2019

(65) Prior Publication Data
US 2019/0262595 A1 Aug. 29, 2019

Related U.S. Application Data

(62) Division of application No. 14/958,227, filed on Dec. 3, 2015, now abandoned.

(51) Int. Cl.
*A61M 25/10* (2013.01)
*B29C 71/02* (2006.01)
(Continued)

(52) U.S. Cl.
CPC ........ *A61M 37/0015* (2013.01); *A61M 25/10* (2013.01); *A61M 25/104* (2013.01);
(Continued)

(58) Field of Classification Search
CPC .... A61J 3/005; A61M 25/10; A61M 25/1029; B29C 71/02
See application file for complete search history.

(56) References Cited

U.S. PATENT DOCUMENTS 5,087,244 A * 2/1992 Wolinsky ............... A61M 25/10
 604/509
5,593,434 A * 1/1997 Williams .................. A61F 2/92
 623/1.36
(Continued)

FOREIGN PATENT DOCUMENTS

JP 4355494 B2 11/2009
JP 2011-513005 A 4/2011
(Continued)

OTHER PUBLICATIONS

KIPO Office Action, dated Feb. 23, 2016, for Korean Application No. 10-2014-0172345 which corresponds to the above-referenced U.S. application.

(Continued)

*Primary Examiner* — Cachet I Proctor
(74) *Attorney, Agent, or Firm* — LRK Patent Law Firm

(57) ABSTRACT

A balloon catheter which is inflated after insertion into a tubular tissue includes: a balloon catheter body made of a polymer material, which is inflatable by fluid injection; and a plurality of microneedles formed on the surface of the balloon catheter body, wherein the microneedles are formed by transferring a biocompatible polymer resin or photocurable resin, filled in intaglio patterns formed on a mold, which have a shape corresponding to a shape of the microneedles, to the surface of the balloon catheter body which is in close contact with the mold, by a thermal molding, thermal crosslinking or photocuring process.

11 Claims, 19 Drawing Sheets

(51) Int. Cl.
*A61M 37/00* (2006.01)
*B29C 49/52* (2006.01)
*B29C 71/04* (2006.01)
*B29C 33/42* (2006.01)
*B29C 33/38* (2006.01)

(52) U.S. Cl.
CPC ... *A61M 25/1029* (2013.01); *A61M 2025/105* (2013.01); *A61M 2025/1031* (2013.01); *A61M 2025/1086* (2013.01); *A61M 2037/0023* (2013.01); *A61M 2037/0053* (2013.01); *B29C 33/3842* (2013.01); *B29C 33/424* (2013.01); *B29C 49/52* (2013.01); *B29C 71/02* (2013.01); *B29C 71/04* (2013.01)

(56) References Cited

U.S. PATENT DOCUMENTS

| | | | | |
|---|---|---|---|---|
| 8,579,956 | B2* | 11/2013 | Hossainy | A61M 25/104 604/103.08 |
| 8,764,712 | B2* | 7/2014 | Melsheimer | A61K 9/0021 604/173 |
| 9,393,386 | B2* | 7/2016 | Schneider | A61M 25/0082 |
| 9,517,122 | B2* | 12/2016 | Firstenberg | A61F 2/848 |
| 2003/0065303 | A1* | 4/2003 | Wellman | A61M 25/1011 604/500 |
| 2004/0098014 | A1* | 5/2004 | Flugelman | A61M 25/104 606/167 |
| 2004/0106904 | A1* | 6/2004 | Gonnelli | A61M 37/0015 604/173 |
| 2007/0213761 | A1* | 9/2007 | Murphy | A61F 2/958 606/194 |
| 2008/0319540 | A1* | 12/2008 | Jordan | A61L 31/14 623/1.49 |
| 2011/0034860 | A1* | 2/2011 | Melsheimer | A61M 37/0015 604/22 |
| 2011/0127690 | A1* | 6/2011 | Honda | A61M 37/0015 264/154 |
| 2011/0160756 | A1* | 6/2011 | Aggerholm | B29C 59/021 606/159 |
| 2012/0130407 | A1* | 5/2012 | Aggerholm | A61B 17/320725 606/159 |
| 2014/0088624 | A1* | 3/2014 | Burton | A61M 25/1002 606/159 |
| 2014/0155927 | A1* | 6/2014 | Burton | A61M 25/104 606/191 |

FOREIGN PATENT DOCUMENTS

| | | |
|---|---|---|
| KR | 10-2002-0059901 A | 7/2002 |
| KR | 10-2006-0048276 A | 5/2006 |
| KR | 10-2010-0129958 A | 12/2010 |
| KR | 10-2012-0019362 A | 3/2012 |
| KR | 10-2013-0133572 A | 12/2013 |
| KR | 10-2014-0006168 A | 1/2014 |

OTHER PUBLICATIONS

KIPO Notice of Allowance, dated Sep. 27, 2016, for Korean Application No. 10-2014-0172345 which corresponds to the above-referenced U.S. application.

* cited by examiner

BALLOON CATHETER HAVING MICRO NEEDLES AND MANUFACTURING METHOD FOR THE SAME

CROSS-REFERENCE TO RELATED APPLICATIONS

The present application is a division of U.S. patent application Ser. No. 14/958,227, filed Dec. 3, 2015, which claimed priority to Korean Patent Application No. 10-2014-0172345, filed Dec. 3, 2014, the disclosure of which are incorporated by reference in their entirety herein.

BACKGROUND OF THE INVENTION

1. Field of the Invention

The present invention relates to a balloon catheter and a method for manufacturing the same, and more particularly, to an invention in which a balloon catheter having microneedles formed thereon can be manufactured in an easy and inexpensive manner by simultaneously transferring microneedles, prepared in intaglio patterns on a mold, to the surface of a balloon catheter body.

2. Description of the Prior Art

Generally, in tubular tissues such as blood vessels, esophagus, intestines, bronchi, airways, bile ducts, urethra, etc., narrowing of blood vessels is caused by arteriosclerosis in blood vessels or by cancer in other organs. For example, in angina patients, vascular narrowing or stenosis occurs in blood vessels, such as coronary arteries or peripheral blood vessels, due to cholesterol buildup, to reduce blood flow, causing severe pain or sudden death. In addition, in the case of bronchogenic cancer, esophageal cancer, bile duct cancer and the like, stenosis caused by tumor mass causes difficult breathing, food intake disorder, digestive disorder or the like, resulting in patient's death. Typical examples of methods for treating such symptoms include angioplasty. As angioplasty, four methods as described below are generally known.

The first method is balloon catheter angioplasty. In this method, a balloon catheter is inserted into a tubular tissue such as a narrowed blood vessel and fixed to a narrowed site, and then the narrowed site is widened by balloon inflation. This method can treat stenosis or occlusion of vessel effectively, but has a problem of high restenosis rate which is higher than 70%.

The second method is a method employing a metal mesh stent, and can reduce the high restenosis rate of the above-described balloon catheter method. Specifically, in this method, a metal mesh stent made of various metals such as stainless steel is inserted into a narrowed tubular tissue to enlarge the tubular tissue to the original size, thereby enabling blood vessels and tubular tissues to maintain their normal function. This method can somewhat overcome the problem of the above-described balloon catheter method, but may cause abnormal growth of vascular smooth muscle cells and immune response-induced blood cell deposition due to stent-induced damage to the inner walls of blood vessels, resulting in neointimal hyperplasia. In addition, this method has a problem in that the rate of restenosis is still as high as 30-40%, and for this reason, repeated reperfusion therapy is required.

The third method is a method employing a drug-eluting stent, and can overcome the problem of neointimal hyperplasia that occurs in the above-described method that uses the metal mesh stent. Specifically, in this method, a drug-eluting stent having an antiproliferative or immunosuppressive drug coated on the surface thereof is applied to a blood vessel so that the coated drug can be absorbed into the blood vessel, thereby preventing both vasoconstriction and neointimal hyperplasia. This method can somewhat overcome the problem of the above-described method employing the metal mesh stent, but has problems in that the drug is lost by blood flow and restenosis can occur due to damage during stent insertion.

The fourth method is a method employing a drug-eluting balloon catheter coated with drugs, and can overcome the problem of the above-described method that uses the drug-eluting stent. Specifically, in this method, a balloon catheter having an antiproliferative or immunosuppressive drug coated on the surface thereof is applied to a blood vessel so that the coated drug can be delivered to the blood vessel, thereby preventing both vasoconstriction and neointimal hyperplasia. This method can somewhat overcome the problems of the above-described method employing the drug-eluting stent. However, like the method employing the drug-eluting stent, the method employing the drug-eluting balloon catheter has a problem of drug loss by blood flow and resulting low delivery efficiency of drug to vascular tissue.

PRIOR ART DOCUMENTS

Patent Document 1: Korean Laid-Open Patent Publication No. 10-2002-0059901 (published on Jul. 16, 2002).

SUMMARY OF THE INVENTION

Accordingly, the present invention has been made in view of the problems occurring in the prior art, and it is an object of the present invention to provide an invention in which a balloon catheter having microneedles formed thereon can be manufactured in an easy and inexpensive manner by simultaneously transferring microneedles, prepared in intaglio patterns on a mold, to the surface of a balloon catheter body.

To achieve the above object, the present invention provides a balloon catheter which is inflated after insertion into a tubular tissue, the balloon catheter comprising: a balloon catheter body made of a polymer material and inflatable by fluid injection; and a plurality of microneedles formed on the surface of the balloon catheter body, wherein the microneedles are formed by transferring a polymer resin or photocurable resin, filled in intaglio patterns formed on a mold, which have a shape corresponding to the shape of the microneedles, to the surface of the balloon catheter body which is in a close contact with the mold, by a thermal molding, thermal crosslinking or photocuring process.

The present invention also provides a method for manufacturing a method for manufacturing a balloon catheter, in which a plurality of microneedles are simultaneously formed on the surface of a balloon catheter body which is inflated after insertion into a tubular tissue, the method comprising: preparing a mold having formed thereon a plurality of intaglio patterns having a shape corresponding to the shape of the microneedles; filling the intaglio patterns with a polymer resin or photocurable resin for forming the microneedles, in which the polymer resin or photocurable resin is transferable to the surface of the balloon catheter body, which is in close contact with the mold, by a thermal molding, thermal crosslinking or photocuring process; arranging the mold so as to surround the balloon catheter body along the circumferential direction of the balloon catheter body while being spaced apart from the balloon catheter body; injecting a fluid into the balloon catheter body to inflate the balloon catheter body to thereby bring the outside surface of the balloon catheter body into contact with the intaglio patterns of the mold; thermally molding or thermally crosslinking the polymer resin filled in the mold or curing the photocurable resin with light energy while maintaining the contact between the balloon catheter body and the mold; and removing the mold from the balloon catheter body, after the microneedles are simultaneously transferred from the inside of the intaglio patterns to the surface of the balloon catheter body.

DETAILED DESCRIPTION OF THE INVENTION

Hereinafter, preferred embodiments of the present invention will be described in detail. The terms or words used in the specifications and claims should not be limited to be construed as usual or dictionary definition but should be rather construed to be consistent with the technical spirits of the present invention.

Throughout the specification, when a first element is referred to as being on a second element, it not only refers to a case where the first element is formed directly on the second element but also a case where a third layer exists between the first element and the second element.

In addition, throughout the specification, when any part is referred to as "including" or "comprising" any component, it does not exclude other components, but may further include or comprise other components, unless otherwise specified.

In addition, alphanumeric identifiers for steps are for ease of explanation and do not indicate the sequential order of steps, and steps may be performed in an order different from a described order unless the context clearly indicates a particular order. In other words, steps may be in the same order as the described order, or may be substantially simultaneously performed, or may be performed in a reverse order.

Figure 1:
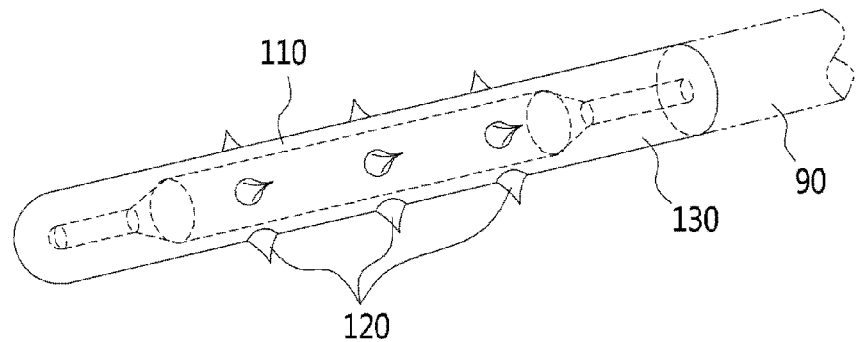
FIG. 1 is a perspective view illustrating a balloon catheter having microneedles formed thereon according to the present invention.
Figure 2:
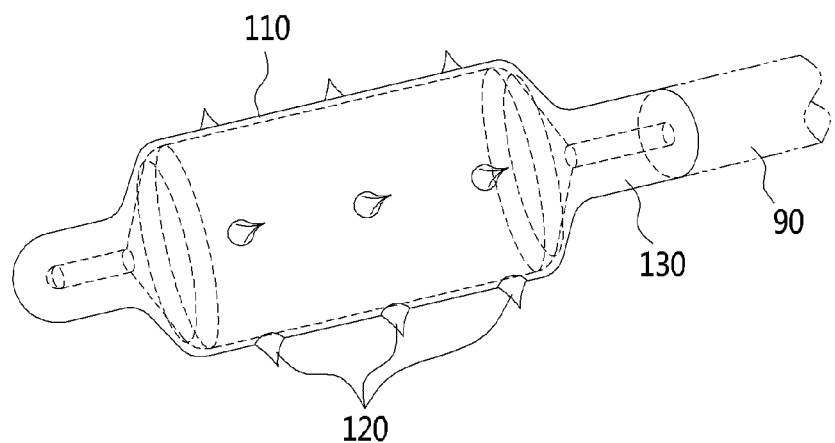
FIG. 2 is a perspective view illustrating a state in which a balloon catheter having microneedles formed thereon according to the present invention is inflated.

FIG. 1 is a perspective view illustrating a balloon catheter having microneedles formed thereon according to the present invention, and FIG. 2 is a perspective view illustrating a state in which the balloon catheter having microneedles formed thereon as shown in FIG. 1 is inflated.

Referring to FIGS. 1 and 2, a balloon catheter 100 comprises: a balloon catheter body 110; one or more microneedles 120 formed on the surface of the balloon catheter body 110; and a fluid injection portion 130 that communicates with the inside of the balloon catheter body 110.

Specifically, as shown in FIG. 2, the balloon catheter body 110 may be made of a polymer material and can be inflated by fluid injection.

In addition, the microneedles 120 may be a material that is the same as or different from that of the balloon catheter body 110, and a plurality of the microneedles 120 are formed on the surface of the balloon catheter body 110 by a simultaneous transfer technique as described below.

Herein, the microneedles 120 are generally made of a material that is harmless to tissue. For example, the microneedles 120 may be made of one or more selected from the group consisting of polytetrafluoroethylenes (e.g., Teflon®), polyethylenes, high-density polyethylenes (HDPEs), polypropylenes, polyurethanes, nylon 6, nylon 12, nylon-based materials, polyalkylene terephthalate, polyester-based materials, thermoplastic polyester elastomers (e.g., Hytrel®), block copolymers consisting of a hard segment of polybutylene terephthalate and a soft amorphous segment based on long-chain polyether glycols, polyimides, polyamide-based materials including polyether-block-copolyamide polymers (e.g., PEBAX®), and PET (polyethylene terephthalate). Particularly, the present invention is characterized by using a polymer resin or photocurable resin which can be transferred from the inside of intaglio patterns, formed on a mold and having a shape corresponding to the shape of microneedles, to the surface of the balloon catheter body 110 which is in close contact with the mold, by a thermal molding, thermal crosslinking or photocuring process, after filling of the resin in the intaglio patterns. This will be described in more detail in the relevant section below.

In some embodiments, the microneedles 120 may be made of a biodegradable polymer material which is different from the material of the balloon catheter body 110 and which can be degraded into harmless components in tissue. Specifically, this biodegradable polymer material may be one or more selected from the group consisting of poly(L-lactic acid), polycaprolactone, poly(lactide-co-glycolide), poly (hydroxybutyrate), poly(hydroxybutyrate-co-valerate), polydioxanone, polyorthoester, polyanhydride, poly (glycotic acid), poly(D, L-lactic acid), poly(glycotic acid co-trimethylene carbonate), polyphosphoester, polyphosphoester urethane, poly(amino acids), cyanoacrylates, poly (trimethylene carbonate), poly(iminocarbonate), copoly (ether-ester), PEO/PLA, polyalkylene oxalates, polyphosphazenes and biomolecules such as fibrin, fibrinogen, cellulose, starch, collagen and hyaluronic acid.

In addition, the biodegradable polymer material may be one or more selected from the group consisting of a mixture of PLGA (poly(lactic/glycolic acid)) and polyethylene glycol, a mixture of PLGA and methoxy polyethylene glycol, and a copolymer of PLGA and methoxy polyethylene glycol.

Meanwhile, the fluid injection portion 90 communicates with the inside of the balloon catheter body 110 so that it can inject a fluid into the balloon catheter body 110.

Furthermore, the outer surface of the microneedles 120 or the outer surface of the balloon catheter body 110, which includes the microneedles 120, may be coated with a drug to be delivered into tissue.

Thus, the balloon catheter 100 comprising this microneedle structure according to the present invention may be used in angioplasty through its insertion into tubular tissues including blood vessels. Also, it can penetrate directly into tissue to effectively deliver a drug to the tissue.

Figure 3:
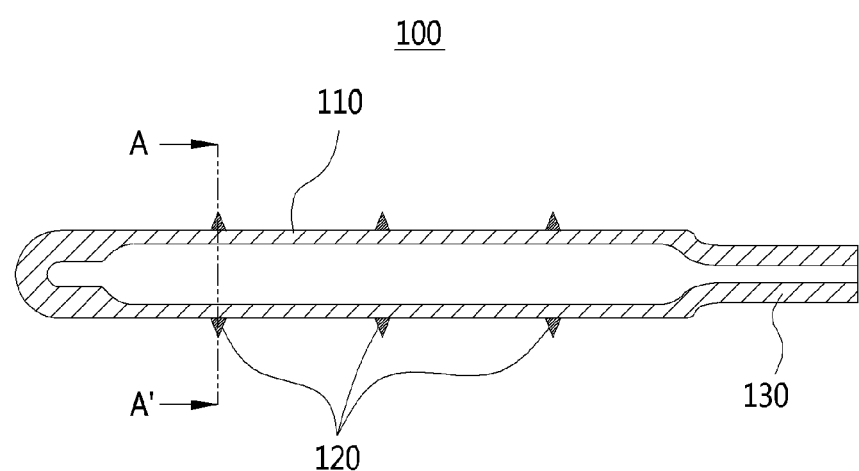
FIG. 3 is a cross-sectional view of the balloon catheter shown in FIG. 1.
Figure 4:
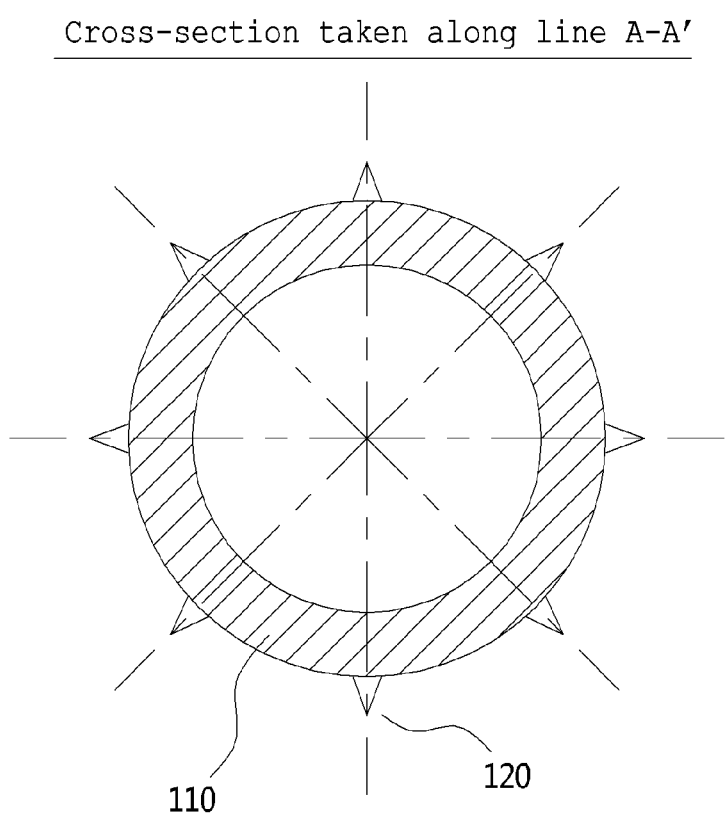
FIG. 4 is a cross-sectional view taken along line A-A' of FIG. 3.

FIG. 3 is a cross-sectional view of the balloon catheter shown in FIG. 1, and FIG. 4 is a cross-sectional view taken along line A-A' of FIG. 3. Referring to FIGS. 3 and 4, the microneedles 120 of the balloon catheter 100 may be arranged in a point or line symmetric manner with respect to the center line of the balloon catheter body 110 as shown in FIG. 4. It is to be understood that the position, spacing or number of microneedles 120 formed may change depending on the shape of a blood vessel or tubular tissue to which the balloon catheter is to be applied.

Figure 5:
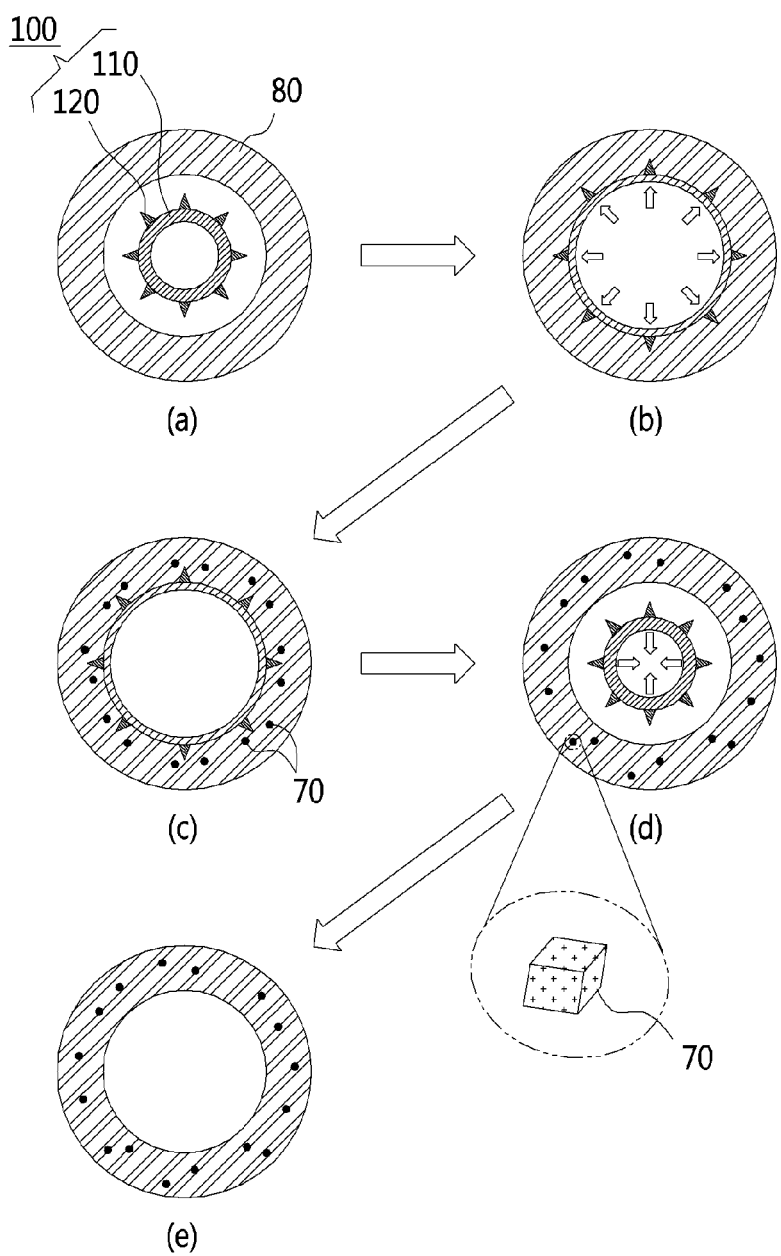
FIG. 5 shows sectional views illustrating a process in which a balloon catheter according to an embodiment of the present invention is inserted into a blood vessel and delivers a drug into tissue.

FIG. 5 shows sectional views illustrating a process in which the balloon catheter is inserted into a blood vessel and delivers a drug into tissue.

As shown in FIG. 5(a), the balloon catheter 100 is inserted into a blood vessel 80 in an uninflated state. Herein, the surface of the microneedles 120 or the outer surface of the balloon catheter body 110 has coated thereon a drug 70 to be delivered into tissue. In addition, as shown in FIG. 5(b), when the balloon catheter body 110 is inflated by injecting a fluid into the balloon catheter 100 inserted into the blood vessel 80, the microneedles 120 come into contact with the surface of the blood vessel or penetrate the blood vessel. Thus, as shown in FIG. 5(c), the drug 70 coated on the surface of the microneedles 120 or the outer surface of the balloon catheter body 110 is penetrated directly into the blood vessel tissue. After a certain period of time, as shown in FIGS. 5(d) and 5(e), the fluid injected into the balloon catheter body 110 is removed to deflate the balloon catheter body 110, and the inserted balloon catheter 100 is removed.

As described above, the balloon catheter 100 having the microneedles 120 formed thereon may be used in angioplasty through its insertion into blood vessels or tubular tissues, and the microneedles 120 can be inserted into tissue to deliver a drug directly into the tissue. Thus, the balloon catheter 100 has a significantly improved effect on drug delivery.

Figure 6:
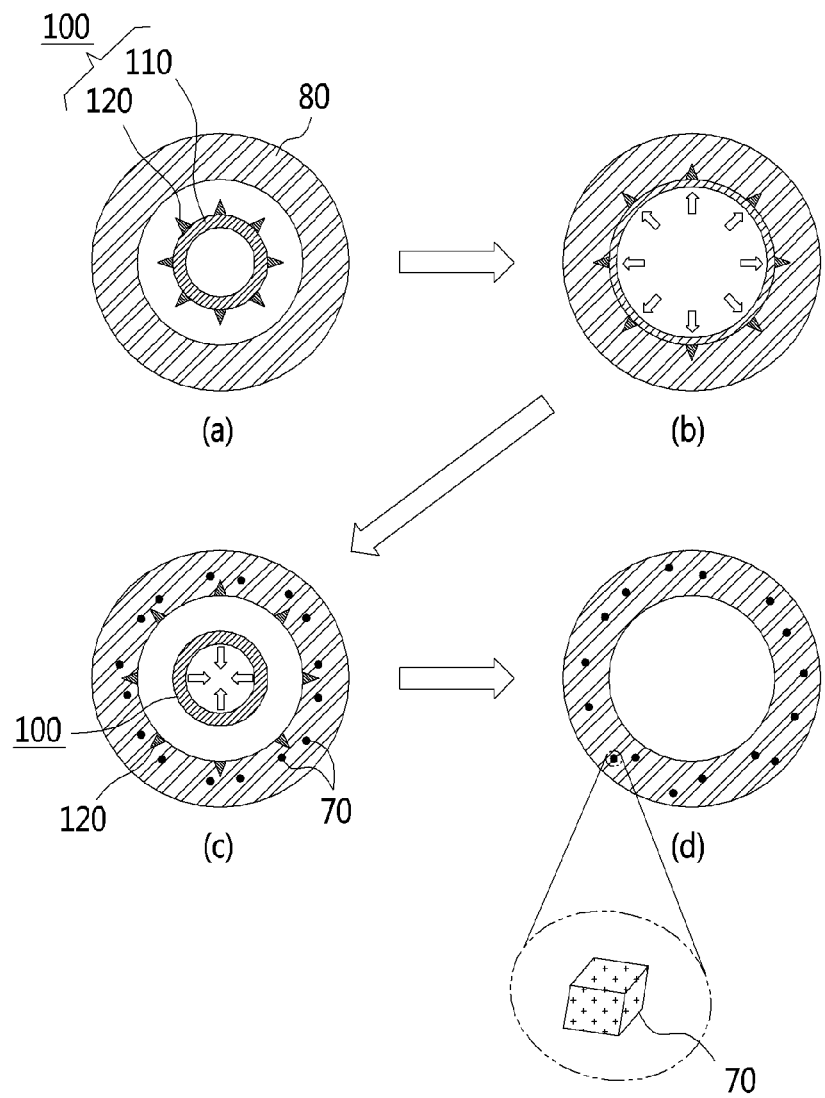
FIG. 6 shows sectional views illustrating a process in which a balloon catheter according to another embodiment of the present invention is inserted into a blood vessel and delivers a drug into tissue.

FIG. 6 shows sectional views illustrating another embodiment in which the balloon catheter 100 is inserted into a blood vessel and delivers a drug into tissue.

As shown in FIG. 6(a), the balloon catheter 100 according to the present invention is inserted into the blood vessel 80 in an uninflated state. Also, as shown in FIG. 6(b), when a fluid is injected into the balloon catheter 100 inserted in the blood vessel 80, the balloon catheter 110 is inflated, and thus the microneedles can come into direct contact with the blood vessel or can penetrate the blood vessel. Next, as shown in FIGS. 6(c) and 6(d), the fluid injected into the balloon catheter body 110 is removed to deflate the balloon catheter 100, and then the balloon 100 is removed.

At this time, as shown in FIG. 6(c), the microneedles 120 are separated from the balloon catheter body 110 and stuck and absorbed in blood vessel tissue 600. In addition, the microneedles 120 are made of a biodegradable polymer material containing a drug 70 to be delivered to tissue 600 such that they can be degraded into harmless components after delivering the drug 70 to the tissue 600.

Thus, in this embodiment, the balloon catheter 100 can be used in angioplasty through its insertion into vascular or tubular tissue, and when a drug is added to microneedles such that it is delivered directly into tissue, the drug delivery effect of the balloon catheter can be significantly increased.

Figure 7:
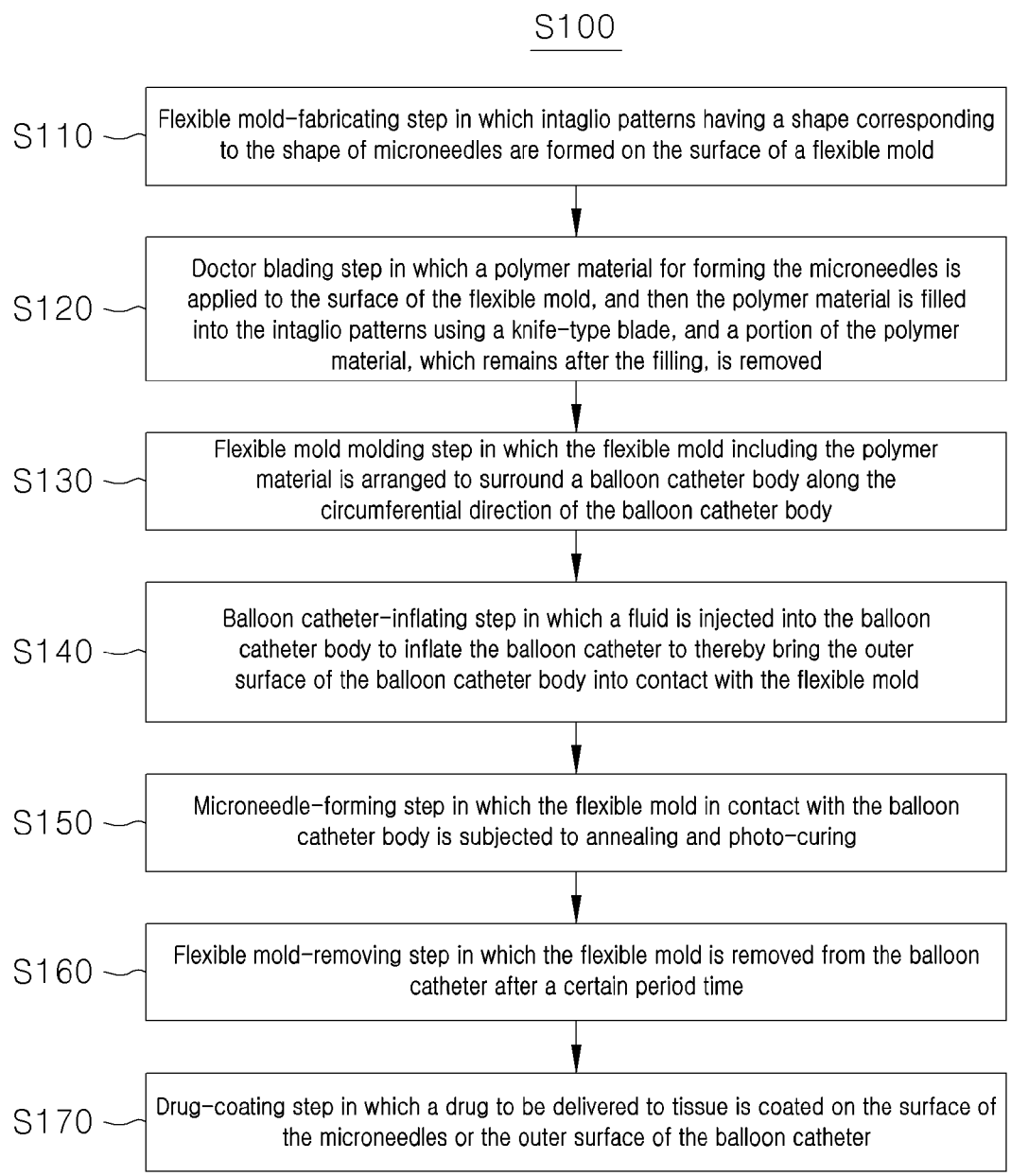
FIG. 7 is a flow chart showing a method for manufacturing a balloon catheter having microneedles formed thereon according to the present invention.
Figure 8:
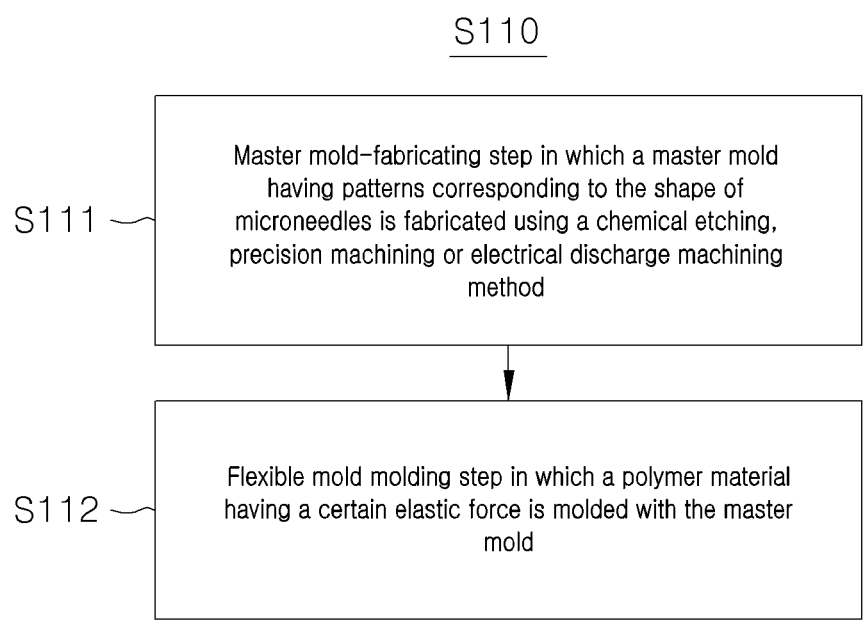
FIG. 8 is a flow chart showing a flexible mold-fabricating step shown in FIG. 7.
Figure 9:
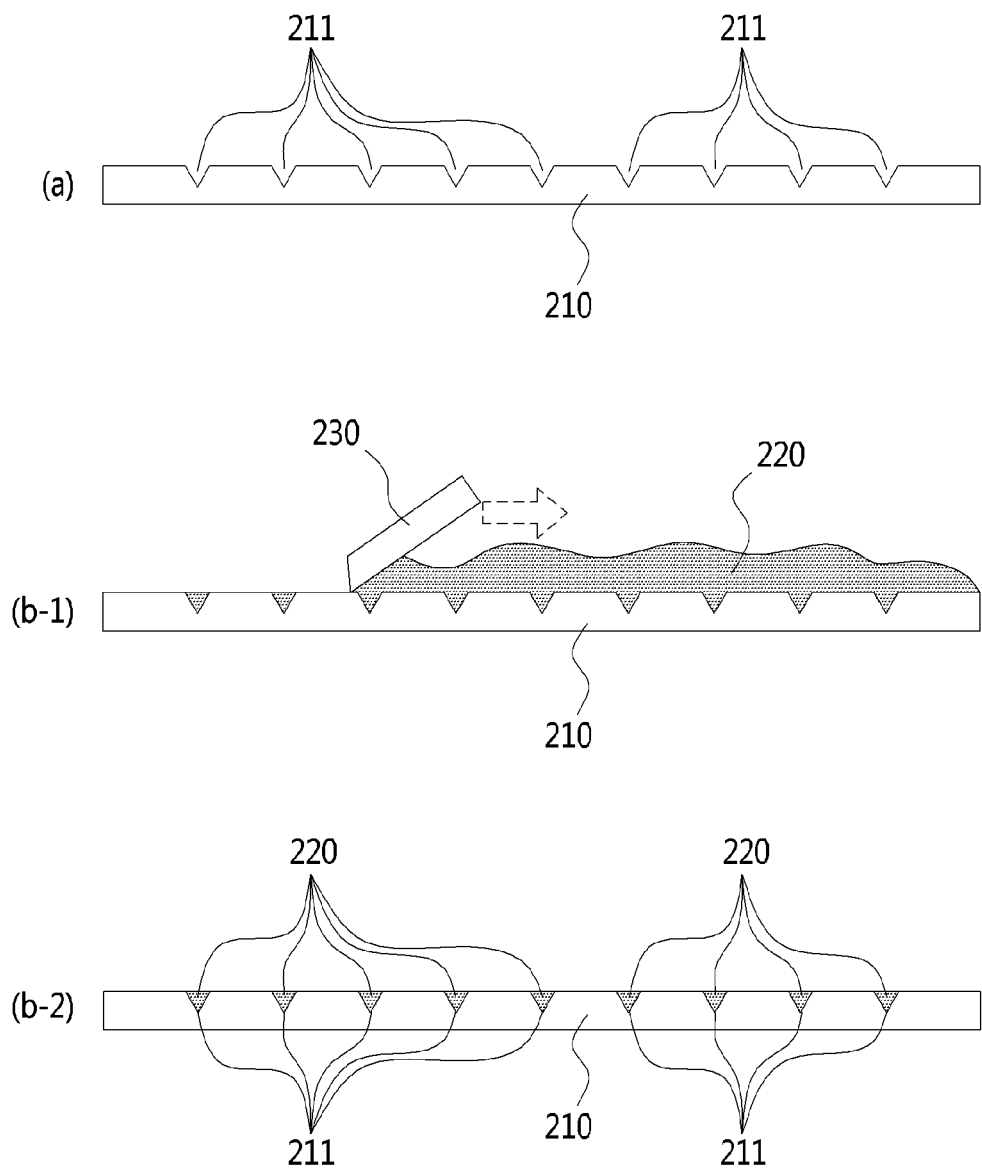
FIGS. 9 to 11 are schematic side views showing a process of forming microneedles according to the present invention.
Figure 10:
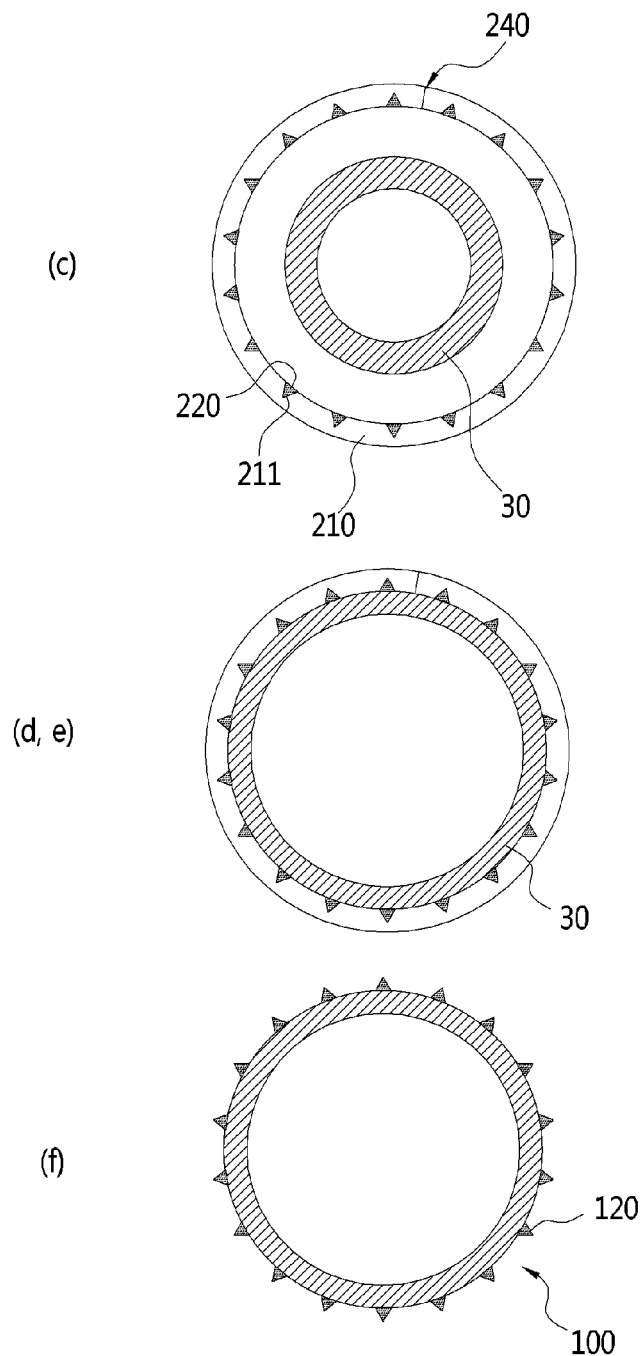
Figure 11:
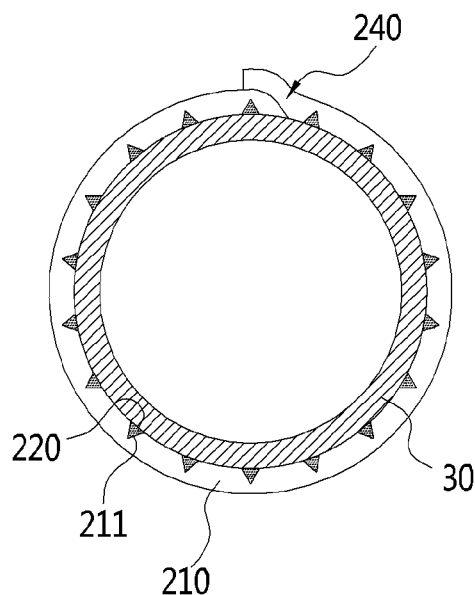
Figure 11:
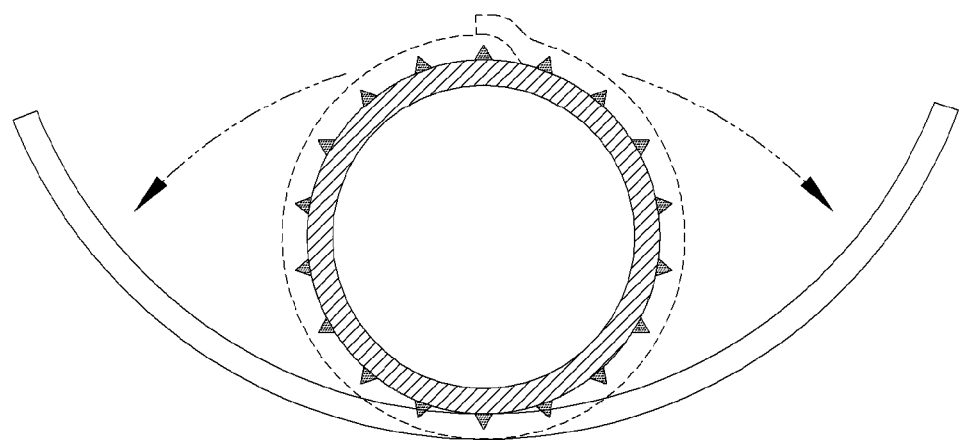
Figure 12:
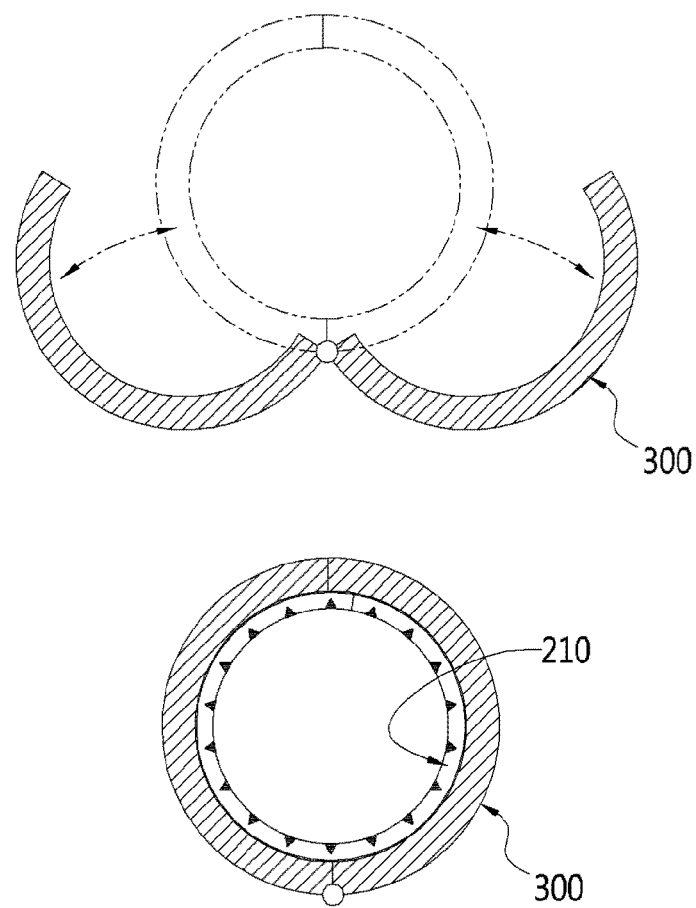
FIG. 12 is a schematic side view showing a state in which a bending jig is used in a process of forming microneedles according to the present invention.

FIG. 7 is a flow chart showing a method for manufacturing a balloon catheter having microneedles formed thereon according to the present invention; FIG. 8 is a flow chart showing a flexible mold-fabricating step shown in FIG. 7; FIGS. 9 to 11 are schematic side views showing a process of forming microneedles according to the present invention, and FIG. 12 is a schematic side view showing a state in which a bending jig is used in a process of forming microneedles according to the present invention.

Hereinafter, a method for manufacturing a balloon catheter having microneedles formed thereon according to an embodiment of the present invention will be described with reference to FIGS. 7 to 12.

A method S100 for manufacturing a balloon catheter 100 according to this embodiment comprises a flexible mold-fabricating step of forming intaglio patterns 211, which correspond to the shape of microneedles, on the surface of a flexible mold 210. Herein, the shape of microneedles may be the shape shown in the figures, but also any of various shapes, for example, a cylindrical shape and a polygonal shape. In addition, it may be a long line shape. Specifically, the shape of microneedles may be any shape that can be inserted into tissue.

Herein, the flexible mold 210 can be fabricated using a master mold. Specifically, as shown in FIG. 8, the flexible mold-fabricating step S110 may comprise a master mold-fabricating step S111 and a flexible mold molding step S112. Herein, the master mold-fabricating step S111 is a process in which a master mold having embossed patterns having a shape corresponding to the shape of microneedles is fabricated by a chemical etching, precision machining or electrical discharge machining method. In addition, the flexible mold molding step S112 is a process in which a polymer material having a certain elastic force is molded using the master mold as a positive mold. Herein, a flexible polymer forming the flexible mold 210 may be one or more selected from the group consisting of poly-dimethylsiloxane (PDMS), poly-caprolactone (PCL), polytetrafluoroethylenes, polyethylenes, high-density polyethylenes (HDPEs), polypropylenes, polyurethanes, nylon 6, nylon 12, nylon-based materials, polyalkylene terephthalate, polyester-based materials, thermoplastic materials, polyester elastomers, block copolymers consisting of a hard segment of polybutylene terephthalate and a soft amorphous segment based on long-chain polyether glycols, polyimides, polyamides including polyether-block-copolyamide polymers, and polyethylene terephthalate (PET).

Furthermore, the flexible mold molding step S112 may also be performed by an electroplating method. Specifically, the flexible mold molding step S112 may also be implemented by depositing a seed layer on the master mold and growing the seed layer by an electroplating method, thereby fabricating a flexible thin metal mold.

In addition, the method S100 for manufacturing the balloon catheter 100 comprises a polymer material-filling step S120 in which the polymer material 220 forming the microneedles is applied to the surface of the flexible mold 210 and then filled into the intaglio patterns by use of a blade-type tool 230. If necessary, the polymer material-filling step S120 may be performed in a vacuum so that the polymer material can be easily filled into the intaglio patterns.

Specifically, as shown in FIG. 9, when the upper surface of the flexible mold 210 is scrapped with the blade-type tool 230 from one end to the other end, the polymer material 220 is filled into the intaglio patterns. The process of scrapping the upper surface of the flexible mold 210 with the blade-type tool 230 may be a doctor blading process.

Herein, the polymer material is applied to the surface of the flexible mold 210 after it is made viscous by heating it to the glass transition temperature or above or dissolving it in a solvent.

Particularly, the polymer material 220 is composed of a material that can be attached to the outer surface of the balloon catheter 30 by thermal molding or thermal crosslinking. In other words, the polymer resin filled in the intaglio patterns, which are formed on the flexible mold and have a shape corresponding to the shape of microneedles, should be composed of a polymer resin that can be transferred from the flexible mold to the surface of the balloon catheter by thermal molding or thermal crosslinking. The polymer material 220 satisfying this condition 220 may be one or more selected from the group consisting of PET (polyethylene terephthalate), PEBAX (polyether block amide) and PLGA (poly(lactic/glycolic acid)).

Alternatively, the polymer material 220 may also be a UV curable resin that is crosslinked or cured by light energy such as UV (ultraviolet) light, or an EB curable resin that is crosslinked or cured by light energy such as EB (electron beam). This light curable resin may include an oligomer, a monomer or a photopolymerization initiator.

Next, as shown in FIG. 10, the method S100 for manufacturing the balloon catheter 100 according to this embodiment comprises a flexible mold-bending step S130 in which the flexible mold 210 having the polymer material 220 filled in the intaglio patterns surrounds the circumference of the balloon catheter 30.

Specifically, the flexible mold 210 is bent such that the intaglio patterns 211 filled with the polymer material 220 face the circular inner portion of the bent flexible mold, and then the balloon catheter 30 is placed in the inner space of the bent flexible mold. As a result, the flexible mold 210 surrounds the balloon catheter 30 is disposed around the balloon catheter 30 along the circumferential direction while it is spaced at a distance from the outer surface of the balloon catheter 30. At this time, as shown in FIG. 10(c), a joint 240 may be formed such that both ends of the flexible mold 210 come in contact with each other. Alternatively, as shown in FIG. 11, the joint 240 may be formed such that both ends of the flexible mold 210 overlap each other. When the joint 240 is formed such that both ends of the flexible mold 210 overlap each other, the bent flexible mold 210 is easily separated in the final step.

In some cases, as shown in FIG. 12, the flexible mold 210 can be stably bent using a bending jig 300. Herein, the bending jig 300 is a cylindrical jig that can be opened in both directions, and may have a hinge structure so that it can be opened and closed. In addition, the bending jig 300 may be made of a plastic or metal material having certain rigidity.

In the case in which the flexible mold 210 is bent using the bending jig 300, when an adhesive is applied between the flexible mold 210 and the inner side of the bending jig 300 to temporarily adhere the flexible mold 210 to the bending jig 300, the flexible mold 210 can be more stably bent.

In addition, as shown in FIG. 10, the method S100 for manufacturing the balloon catheter 100 according to this embodiment comprises a balloon catheter-inflating stem S140 in which a fluid is injected into the balloon catheter body so that the outer surface of the balloon catheter 30 comes into contact with the flexible mold 210.

Specifically, when the balloon catheter 30 is disposed in the inner space of the round bent flexible mold 210 and inflated, the outer surface of the balloon catheter 30 comes into contact with the inside of the round bent flexible mold 210. Herein, the polymer material 220 filled in the intaglio patterns of the flexible mold 210 can be brought into contact with the outer surface of the balloon catheter 30 by maintaining the inflated state of the balloon catheter 30.

This is followed by a microneedle-forming step S150 in which the flexible mold 210 in contact with the balloon catheter body is subjected to thermal molding, thermal crosslinking or photo-curing. Specifically, when the polymer material 220 in contact with the outer surface of the balloon catheter 30 is subjected to a thermal molding, thermal crosslinking or photo-curing process, the microneedle-shaped polymer material 220 filled in the intaglio patterns of the flexible mold 210 adheres to the outer surface of the balloon catheter 30.

In the case in which the microneedle-forming step S150 is performed by thermal molding or thermal crosslinking, the balloon catheter 30 and the flexible mold 210 are maintained at a temperature between 50° C. and 200° C. for a few minutes to a few tens of minutes. In the case in which the microneedle-forming step S150 is performed by photo-curing, the balloon catheter 30 and the flexible mold 210 are exposed to light energy such as UV light or an electron beam for a few minutes to a few tens of minutes.

Next, after a certain period of time, a flexible mold-removing step S160 is performed in which the flexible mold 210 is removed from the balloon catheter 30. Through the microneedle-forming step S150, the polymer material 220 filled in the intaglio patterns of the flexible mold is transferred to the outer surface of the balloon catheter 30 to form microneedles.

According to the method S100 for manufacturing the balloon catheter 100 in accordance with the embodiment illustrated in FIG. 10, microneedles can be simultaneously transferred throughout the outer surface of the balloon catheter 30, and thus the balloon catheter having microneedles formed thereon can be manufactured in a simpler and more inexpensive manner compared to a conventional method in which microneedles are formed one by one.

In addition, according to this embodiment, the outer surface of the balloon catheter and the intaglio patterns of the flexible mold are brought into contact with one another for microneedle transfer by injecting a fluid into the balloon catheter to inflate the balloon catheter, and thus the mold and the balloon catheter body do not need to be aligned with each other with high precision. In addition, because the flat flexible mold is rolled and disposed to surround the balloon catheter, the circumferential spacing (angle) of microneedles that are formed on the surface of the balloon catheter if the diameter of the rolled flexible mold having uniform intaglio patterns formed thereon is changed. Thus, this embodiment is very useful for manufacturing balloon catheters having various configurations.

In addition, the method according to this embodiment may further comprise a drug coating step S170 in which a drug to be delivered is coated on the surface of the formed microneedles 120 or the outer surface of the balloon catheter 100, which includes the microneedles.

Figure 13:
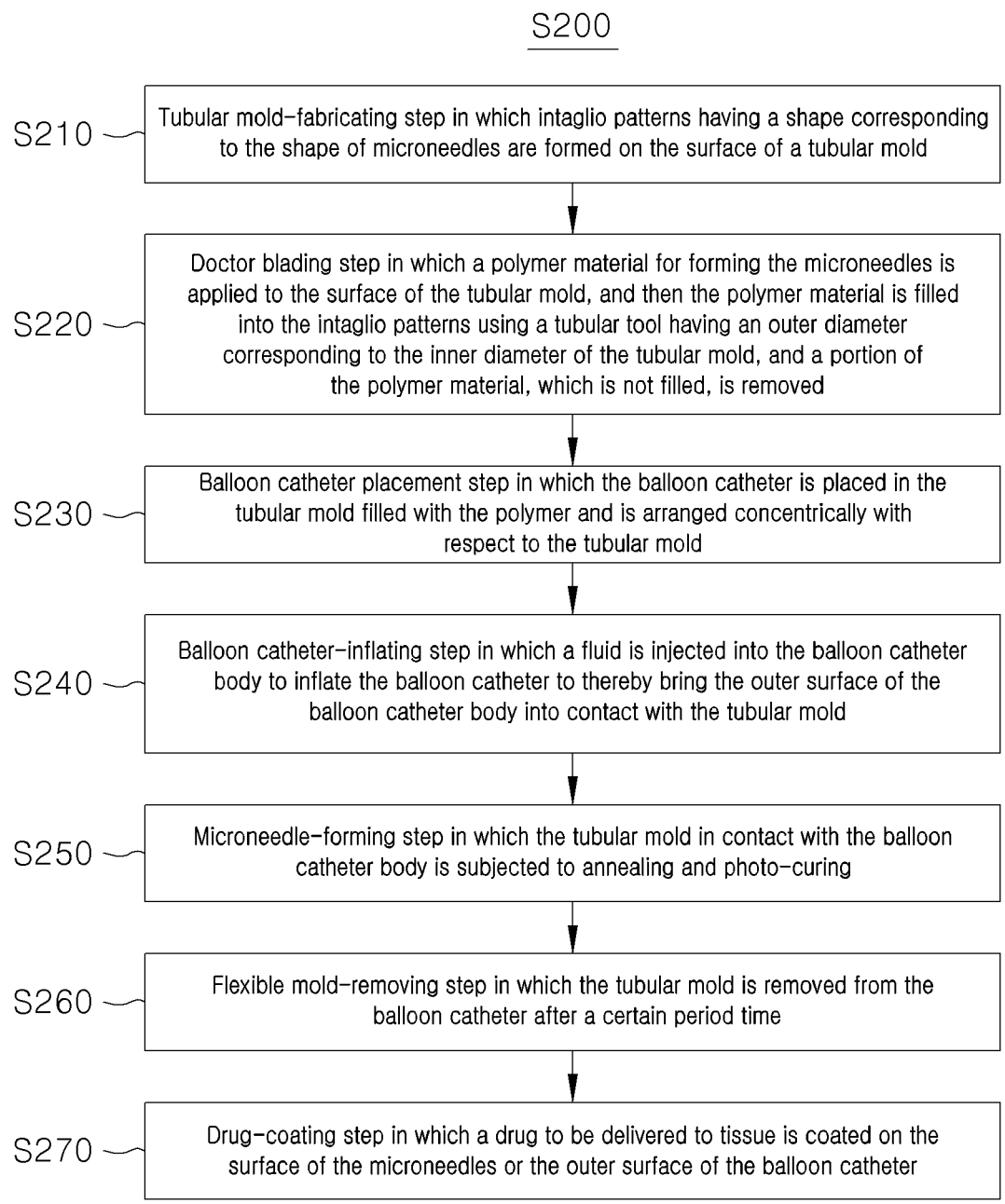
FIG. 13 is a flow chart showing a method for manufacturing a balloon catheter having microneedles formed thereon according to another embodiment of the present invention.
Figure 14:
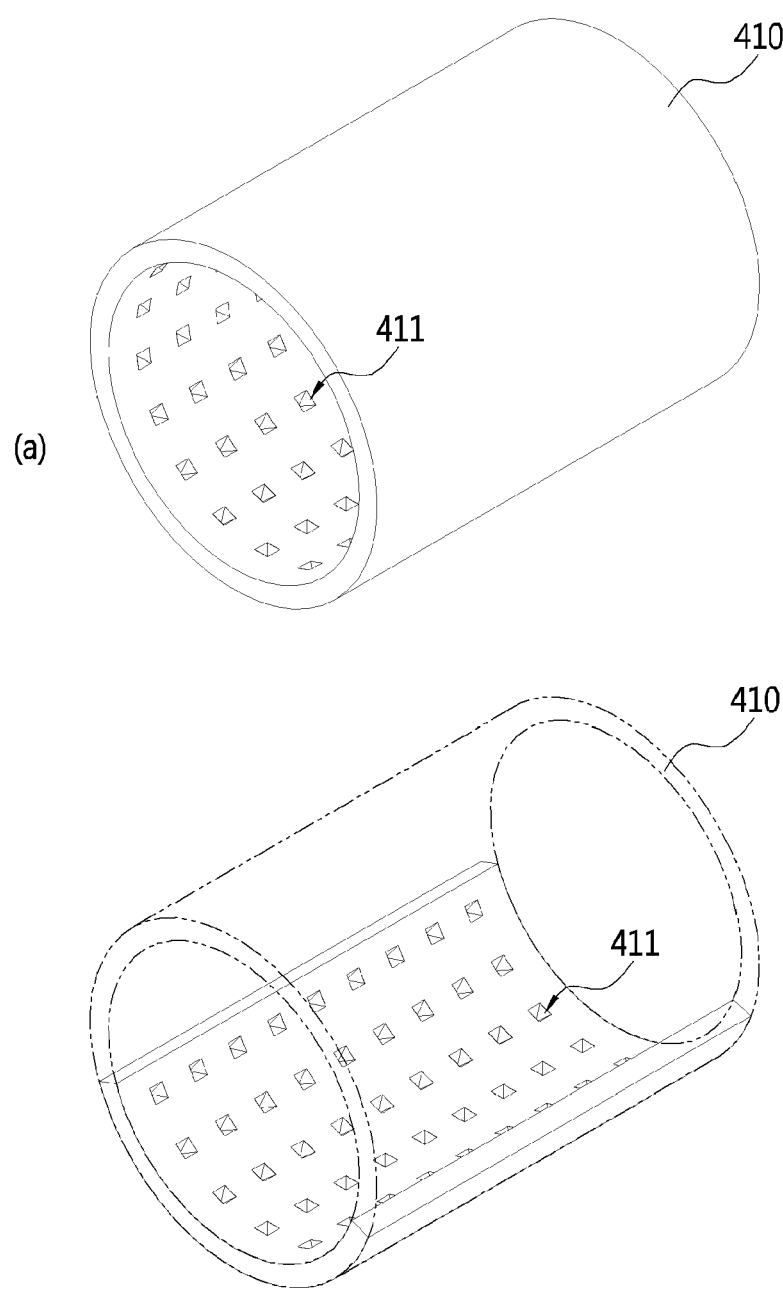
FIGS. 14 to 16 are schematic views showing a process of forming microneedles according to the present invention.
Figure 15:
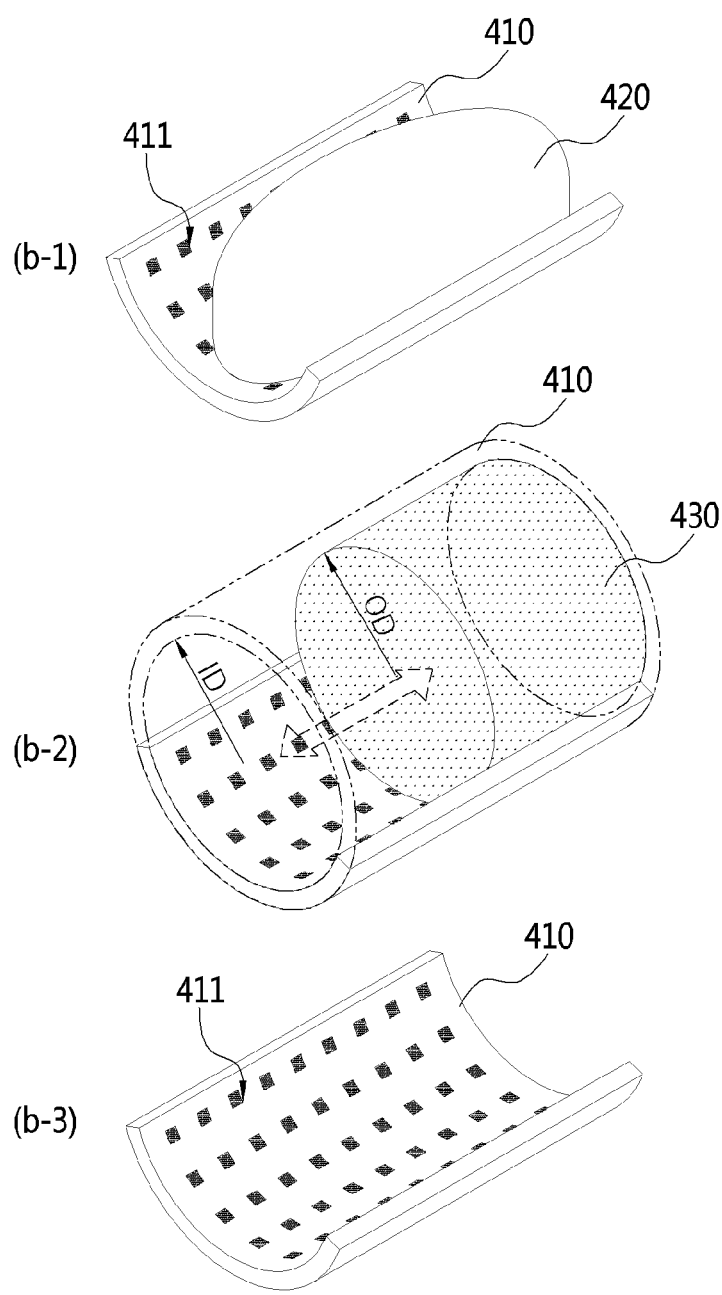
Figure 16:
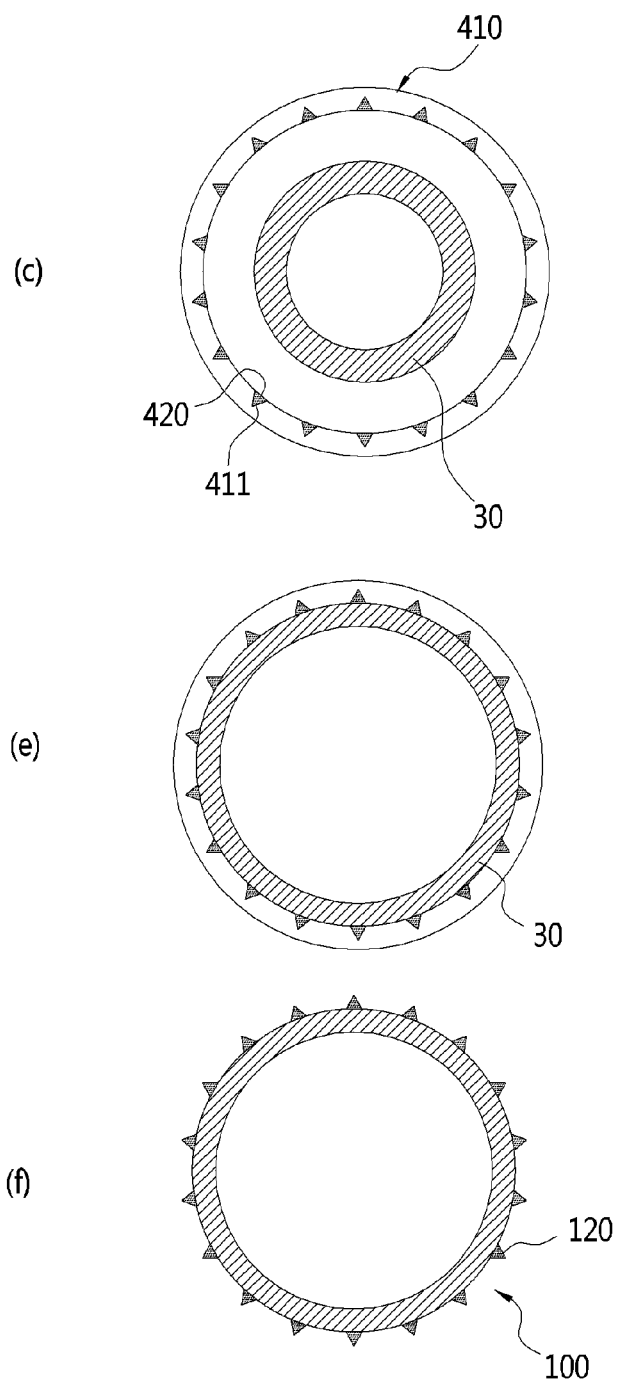

Meanwhile, FIG. 13 is a flow chart showing a method for manufacturing a balloon catheter having microneedles formed thereon according to another embodiment of the present invention, and FIGS. 14 to 16 are schematic views showing a process of forming microneedles according to the present invention.

Referring to FIGS. 13 to 16, a balloon catheter manufacturing method S200 according to this embodiment comprises a tubular mold-fabricating step S210, a doctor blading step S220, a balloon catheter placement step S230, a balloon catheter-inflating step S240, a microneedle-forming step S250, and a tubular mold-removing step S260.

Specifically, as shown in FIG. 14, the tubular mold-forming step S210 is a step in which intaglio patterns 411 having a shape corresponding to the shape of microneedles are evenly formed on the inner surface of a tubular mold 410. This step will be described in detail in the relevant section below.

As shown in FIG. 15, the doctor blading step S220 is a step in which a polymer material 420 forming microneedles is applied to the inner surface of the tubular mold 410, and then the polymer material is filled into the intaglio patterns by use of a cylindrical tool having an outer diameter (OD) corresponding to the inner diameter (ID) of the tubular mold 410 while the remaining polymer material is removed. In FIG. 15, the entire shape of the tubular mold 410 is not shown, and only half of the tubular mold 420 is shown so that the internal appearance of the tubular mold 420 can be more easily understood.

As shown in FIG. 16, the balloon catheter placement step S230 is a step in which a balloon catheter 30 is placed in the tubular mold 410 filled with the polymer and is disposed concentrically with respect to the tubular mold 410.

The balloon catheter-inflating step S240 is a step in which a fluid is injected into a balloon catheter body to inflate the balloon catheter 30 to thereby bring the outer surface of the balloon catheter 30 into contact with the tubular mold 410.

The microneedle-forming step S250 is a step in which the tubular mold 410 in contact with the balloon catheter body is subjected to thermal molding, thermal crosslinking or photo-curing. Herein, the thermal molding, thermal crosslinking or photo-curing process is as described above.

In addition, the tubular mold-removing step S260 is a step in which the tubular mold 410 is removed from the balloon catheter 30 after a certain period of time.

Hereinafter, the method for fabricating the tubular mold 410 will be described in detail.

Figure 17:
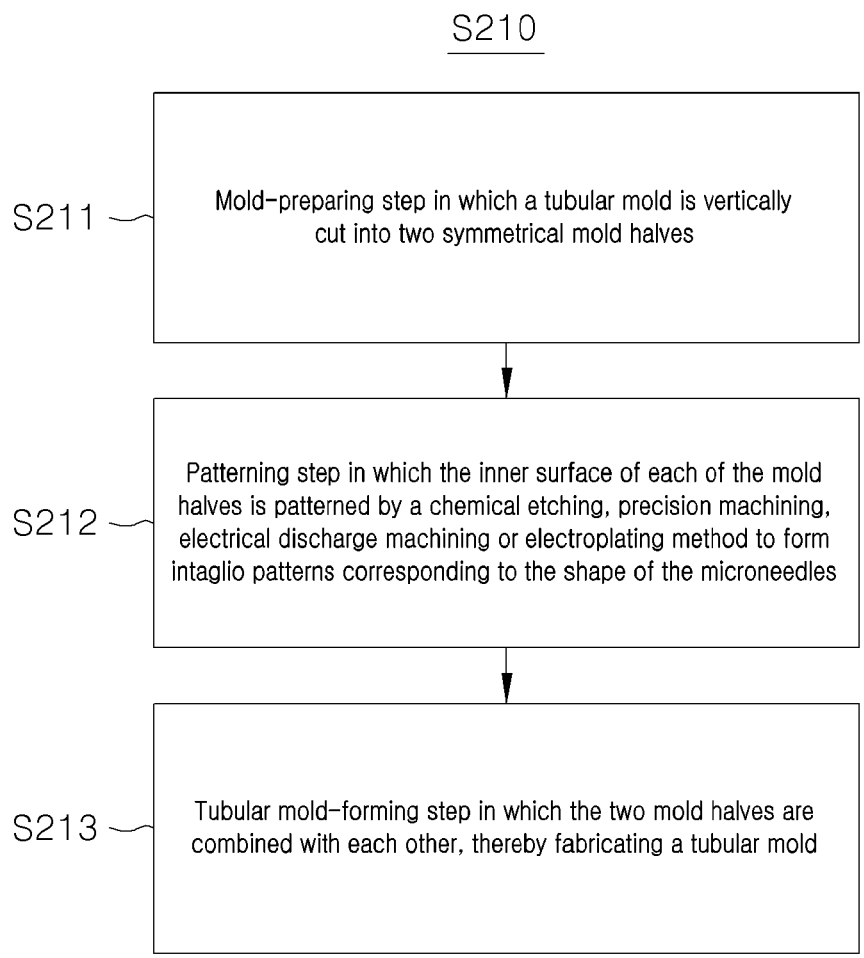
FIG. 17 is a flow chart showing a tubular mold-fabricating step shown in FIG. 13.
Figure 18:
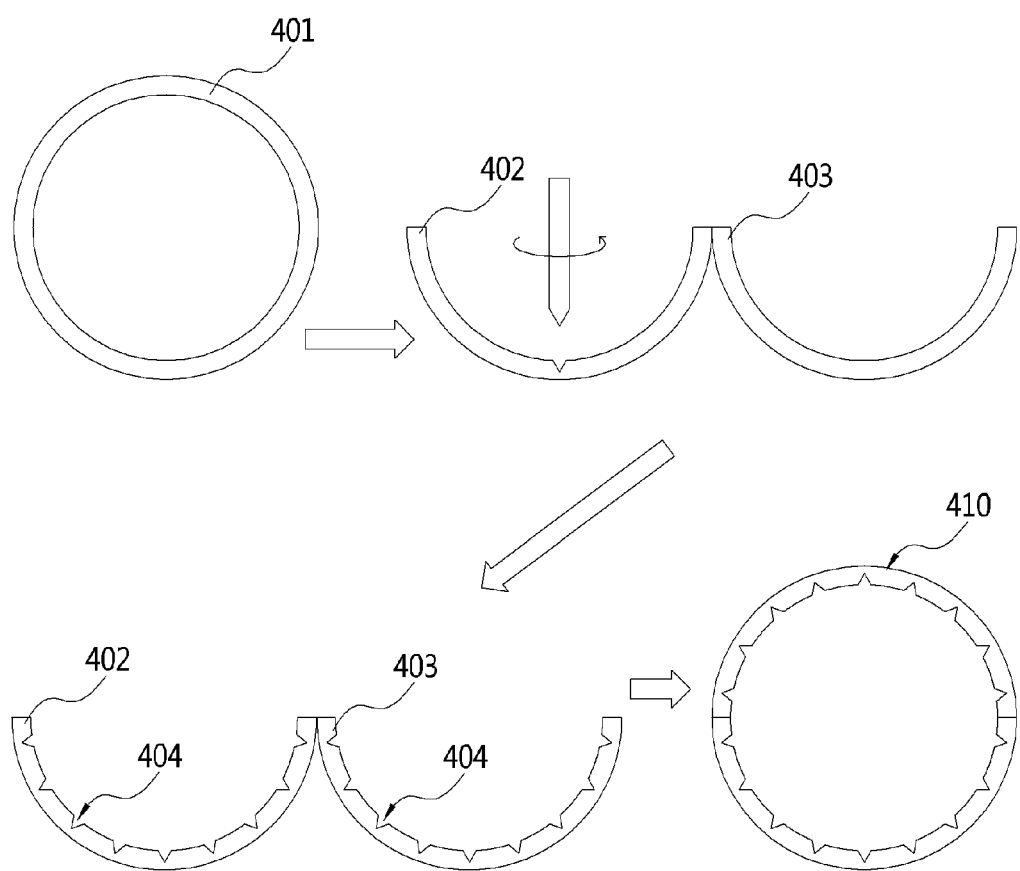
FIG. 18 is a schematic side view showing a process in which a tubular mold is fabricated according to a tubular mold-fabricating step shown in FIG. 17.

FIG. 17 is a flow chart showing the tubular mold-fabricating step shown in FIG. 13, and FIG. 18 is a schematic side view showing a process in which the tubular mold is fabricated according to the tubular mold-fabricating step shown in FIG. 17.

Referring to FIGS. 17 and 18, the tubular mold 410 according to this embodiment can be fabricated through the steps of:

a-1) a mold-preparing step (S211) in which a tubular mold 401 is vertically cut into two symmetrical mold halves 402 and 403;

a-2) a patterning step (S212) in which the inner surface of each of the mold halves 402 and 403 is patterned by a chemical etching, precision machining, electrical discharge machining or electroplating method to form intaglio patterns having a shape corresponding to the shape of the microneedles; and a-3) a tubular mold-forming step (S213) in which the two mold halves 402 and 403 are combined with each other, thereby fabricating a tubular mold 410.

Figure 19:
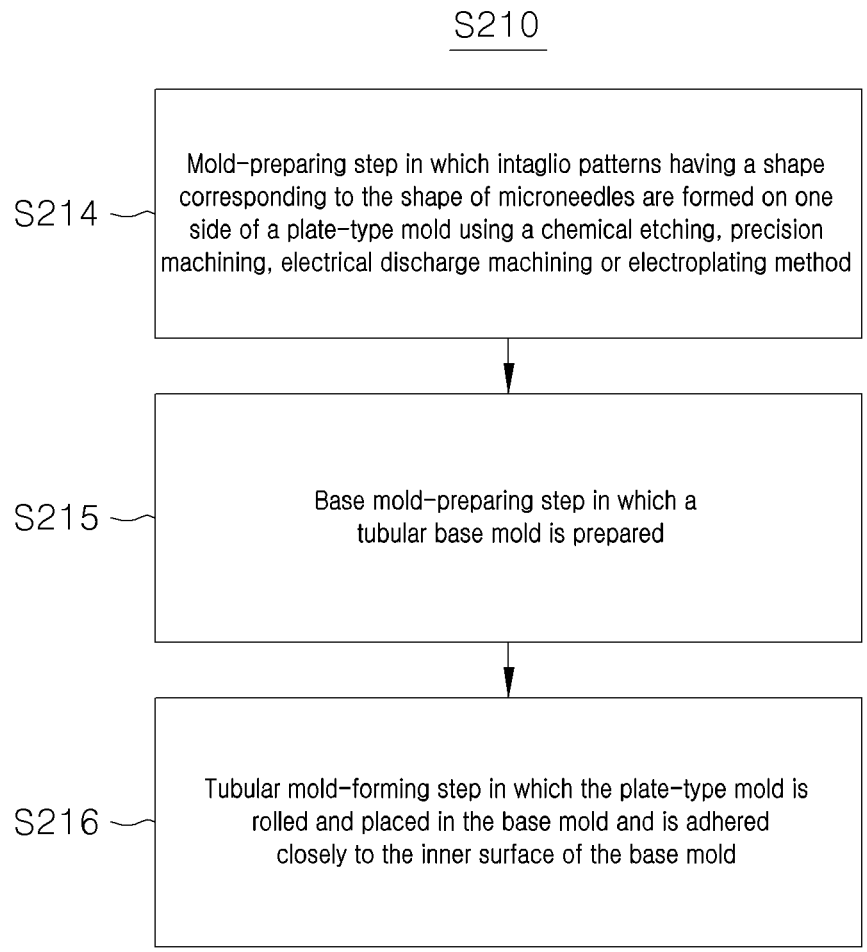
FIG. 19 is a flow chart showing a tubular mold-fabricating step shown in FIG. 13.
Figure 20:
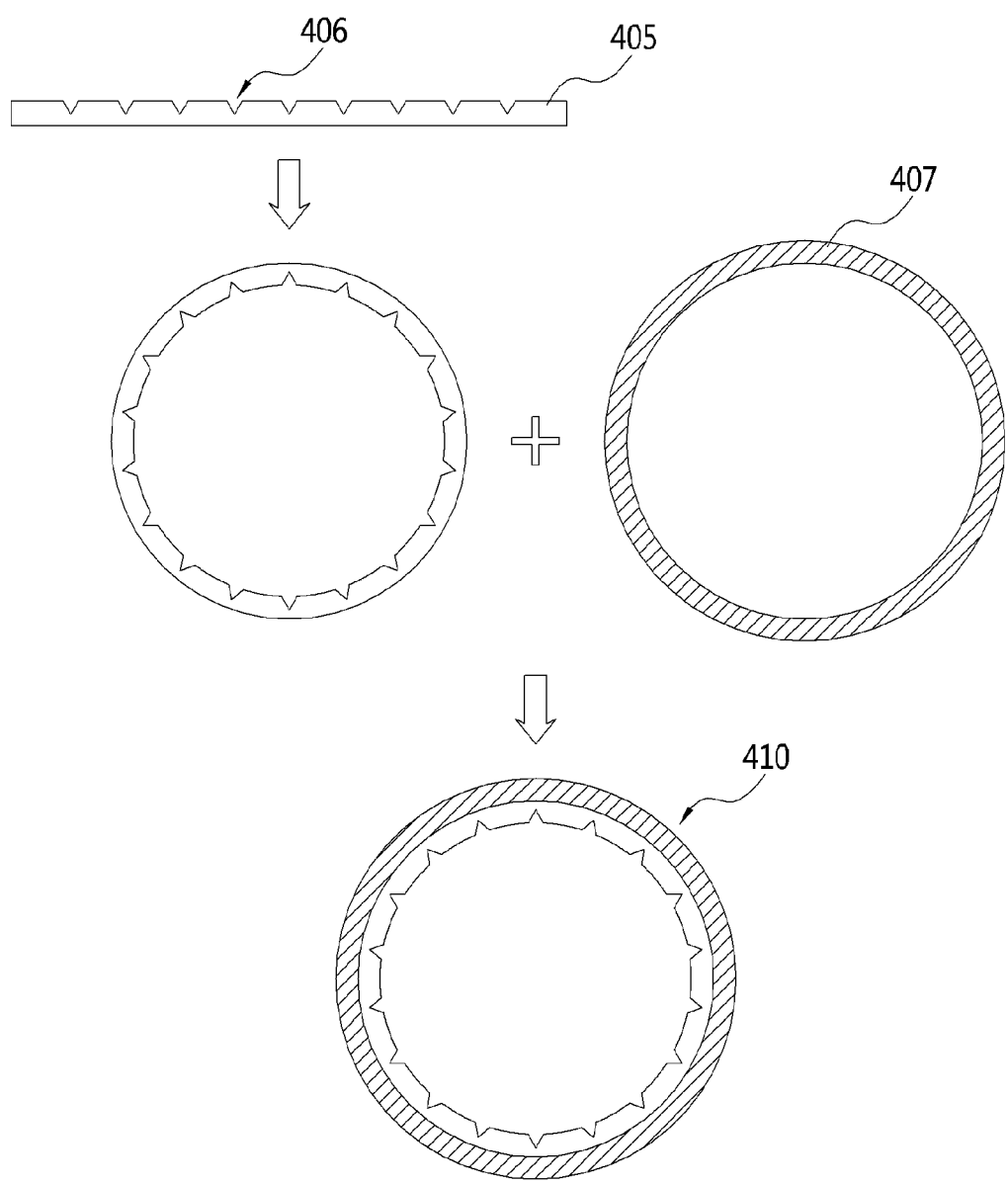
FIG. 20 is a schematic side view showing a process in which a tubular mold is fabricated according to a tubular mold-fabricating step shown in FIG. 19.

FIG. 19 is a flow chart showing the tubular mold-fabricating step shown in FIG. 13, and FIG. 20 is a schematic side view showing a process in which a tubular mold is fabricated according to the tubular mold-fabricating step shown in FIG. 19.

As shown in FIGS. 19 and 20, the tubular mold 410 according to this embodiment is fabricated through the steps of:

b-1) a mold-preparing step (S214) in which intaglio patterns 406 having a shape corresponding to the shape of microneedles are formed on one side of a plate-type mold 405 using a chemical etching, precision machining, electrical discharge machining or electroplating method;

b-2) a base mold-preparing step (S215) in which a tubular base mold 407 is prepared; and b-3) a tubular mold-forming step (S216) in which the plate-type mold 405 is rolled and placed in the base mold 407 and is adhered closely to the inner surface of the base mold 407.

As described above, according to the balloon catheter manufacturing method of this embodiment, a plurality of microneedles can be easily formed on the surface of a balloon catheter by a simultaneous transfer technique.

As described above, according to the inventive balloon catheter having microneedles formed thereon and the method for manufacturing the balloon catheter, a plurality of microneedles can be formed at the same time by simultaneously transferring microneedles, prepared in intaglio patterns on a mold, to the surface of a balloon catheter body. Thus, the balloon catheter having microneedles formed thereon can be produced in a simple and inexpensive manner.

In addition, according to the present invention, the outer surface of the balloon catheter body and the intaglio patterns of the mold are brought into contact with one another for microneedle transfer by injecting a fluid into the balloon catheter body to inflate the balloon catheter body, and thus the mold and the balloon catheter do not need to be aligned with each other with high precision. Furthermore, in the case in which a flat flexible mold is rolled and arranged to surround the balloon catheter, the circumferential spacing (angle) of microneedles that are formed on the surface of the balloon catheter can be changed if the diameter of the rolled flexible mold is changed. Thus, the present invention is highly useful for manufacturing various balloon catheters.

What is claimed is:

1. A method for manufacturing a balloon catheter, in which a plurality of microneedles are simultaneously formed on a surface of a balloon catheter body which is inflated after insertion into a tubular tissue, the method comprising:
- preparing a mold having formed thereon a plurality of intaglio patterns having a shape corresponding to a shape of the microneedles;
- filling the intaglio patterns with a biocompatible polymer resin or photocurable resin for forming the microneedles, in which the polymer resin or photocurable resin is transferable to the surface of the balloon catheter body, which is in close contact with the mold, by a thermal molding, thermal crosslinking or photo-curing process;
- arranging the mold so as to surround the balloon catheter body along a circumferential direction of the balloon catheter body while being spaced apart from the balloon catheter body;
- injecting a fluid into the balloon catheter body to inflate the balloon catheter body to thereby bring an outside surface of the balloon catheter body into contact with the intaglio patterns of the mold;
- thermally molding or thermally crosslinking the polymer resin filled in the mold or curing the photocurable resin with light energy while maintaining the contact between the balloon catheter body and the mold; and
- removing the mold from the balloon catheter body, after the microneedles are simultaneously transferred from the inside of the intaglio patterns to the surface of the balloon catheter body through the thermal molding, thermal crosslinking or curing of the polymer.

2. The method of claim 1, wherein the mold is a flexible mold, in which the flexible mold is rolled into a circular shape and arranged so as to surround the balloon catheter body along a circumferential direction of the balloon catheter body while being spaced apart from the balloon catheter body.

3. The method of claim 2, wherein the flexible mold is fabricated by fabricating a master mold having embossed patterns having a shape corresponding to the shape of the microneedles by use of a chemical etching, machining or electrical discharge machining method and, and molding an elastic polymer material on the mold.

4. The method of claim 2, wherein the flexible mold is fabricated by fabricating a master mold having embossed patterns having a shape corresponding to the shape of the microneedles by use of a chemical etching, machining or electrical discharge machining method, depositing a seed layer on the master mold, and growing the seed layer by electroplating.

5. The method of claim 1, wherein the mold is a tubular mold having a circular cross-section.

6. The method of claim 5, wherein the tubular mold is made by forming the intaglio patterns on an inner surface of each of two mold halves having a semicircular shape, and combining the two mold halves.

7. The method of claim 2, wherein the polymer resin or photocurable resin is applied to the flexible mold in a state in which the flexible mold is flat, and then the polymer resin or photocurable resin is filled into the intaglio patterns using a doctor blade, and a portion of the resin, which remains after the filling, is removed.

8. The method of claim 5, wherein the polymer resin or photocurable resin is applied to an inner surface of the tubular mold, and then a cylindrical tool having an outer diameter corresponding to an inner diameter of the tubular mold is pushed into the tubular mold to fill the polymer resin or photocurable resin into the intaglio patterns while a portion of the resin, which is not filled, is removed.

9. The method of claim 1, wherein the surface or inside of the microneedles transferred to the surface of the balloon catheter body contains a drug to be delivered to the tubular tissue.

10. The method of claim 1, wherein the polymer resin is at least one resin selected from the group consisting of biocompatible and thermally formable polymers.

11. The method of claim 1, wherein the photocurable resin includes an oligomer, a monomer and a photopolymerization initiator and is crosslinked or cured by application of light energy selected from the group consisting of UV light and an electron beam.

* * * * *